(12) United States Patent
Xue et al.

(10) Patent No.: US 11,853,663 B2
(45) Date of Patent: Dec. 26, 2023

(54) MONTE CARLO MOLECULAR SIMULATION METHOD FOR EFFICIENT CALCULATION OF THE INTERFACIAL TENSION OF WATER/BENZENE LIQUID PHASE BY IMPROVING EWALD SUM

(71) Applicant: SHENZHEN JINGTAI TECHNOLOGY CO., LTD., Guangdong (CN)

(72) Inventors: Bai Xue, Guangdong (CN); Jian Ma, Guangdong (CN); Lipeng Lai, Guangdong (CN); Shuhao Wen, Guangdong (CN); Peiyu Zhang, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 499 days.

(21) Appl. No.: 17/055,605

(22) PCT Filed: Oct. 17, 2019

(86) PCT No.: PCT/CN2019/111632
§ 371 (c)(1),
(2) Date: Nov. 16, 2020

(87) PCT Pub. No.: WO2020/228238
PCT Pub. Date: Nov. 19, 2020

(65) Prior Publication Data
US 2021/0365618 A1    Nov. 25, 2021

(51) Int. Cl.
*G06F 30/28* (2020.01)
*G06N 7/01* (2023.01)

(52) U.S. Cl.
CPC ............. *G06F 30/28* (2020.01); *G06N 7/01* (2023.01)

(58) Field of Classification Search
CPC ...... G06F 30/28; G06F 30/25; G06F 2111/08; G06F 2113/08; G06N 7/01; G16C 20/30; G16C 10/00
See application file for complete search history.

(56) References Cited

FOREIGN PATENT DOCUMENTS

| CN | 104715096 | 6/2015 |
| CN | 105468905 | 4/2016 |

(Continued)

OTHER PUBLICATIONS

Per Linse, "Monte Carlo simulation of liquid-liquid benzene-water interface," J. Chem. Phys. 86, 4177 (1987) (Year: 1987).*

(Continued)

*Primary Examiner* — Steven W Crabb
(74) *Attorney, Agent, or Firm* — MUNCY, GEISSLER, OLDS & LOWE, P.C.

(57) ABSTRACT

The disclosure provides an efficient Monte Carlo molecular simulation method for calculating the liquid phase interfacial tension between benzene and water by improving Ewald sum, including the following steps: Step A: Initialize the simulation: two simulation boxes were prepared, both with the size (30×30×45 Å)-(35×35×55 Å), and 1200-2000 water molecules and 230-380 benzene molecules were respectively put on the grid point of the two boxes; Step B: Select the force field used for simulation; Step C: Perform Monte Carlo simulations on the two boxes separately under the canonical ensemble; Step D: Join the water box and the benzene box along the z direction to form a large box of (30×30×90 Å)-(35×35×110 Å), and run 50000-80000 Monte Carlo cycles to make the system reach equilibrium; Step E: After the system reaches equilibrium, the data was collected during the production period.

8 Claims, 2 Drawing Sheets

(56) References Cited

FOREIGN PATENT DOCUMENTS

CN      108829919      11/2018
WO      2008115934      9/2008

OTHER PUBLICATIONS

Aziz Ghoufi et al., "Computer modelling of the surface tension of the gas-liquid and liquid-liquid interface," Chem. Soc. Rev., 45, 1387 (2016) (Year: 2016).*
Michael P. Allen et al., "Computer Simulation of Liquids", Oxford university press, Jun. 22, 2017, pp. 1-2.
Susana Zeppieri et al., "Interfacial Tension of Alkane + Water Systems", J. Chem. Eng., Jun. 12, 2001, pp. 1086-1088.
G. Wiegand et al., "Interfacial tension between water and non-polar fluids up to 473 K and 2800 bar", Ber. Bunsen. Phys. Chem., Jun. 1994, pp. 809-817.
Harley Y. Jennings, Jr., "The Effect of Temperature and Pressure on the Interfacial Tension of Benzene-Water and Normal Decane Water", Journal of Colloid and Interface Science, Jul. 1967, pp. 323-329.
"International Search Report (Form PCT/ISA/210) of PCT/CN2019/111632," dated Jul. 15, 2020, pp. 1-6.

* cited by examiner

MONTE CARLO MOLECULAR SIMULATION METHOD FOR EFFICIENT CALCULATION OF THE INTERFACIAL TENSION OF WATER/BENZENE LIQUID PHASE BY IMPROVING EWALD SUM

CROSS-REFERENCE TO RELATED APPLICATION

This application is a 371 of international application of PCT application serial no. PCT/CN2019/111632, filed on Oct. 17, 2019. The entirety of each of the above-mentioned patent applications is hereby incorporated by reference herein and made a part of this specification.

BACKGROUND

Technical Field

The disclosure pertains to the field of molecular simulation. It concerns a more efficient approach to run Monte Carlo simulations. It can be especially applied in a variety of simulations, such as the simulations of phase equilibrium, thermodynamic properties, and etc.

Description of Related Art

With the development of computers, molecular simulation has become an increasingly popular subject. Molecular simulations can simulate a variety of physical and chemical process with the help of computer and has the potential to replace traditional experimental methods. However, the computing power of computers still limits the size of the system that a molecular simulation can simulate. Therefore, the development of more efficient molecular simulation methods has become an important task. There are two types of traditional molecular simulation methods, the Monte Carlo simulation and the Molecular Dynamics simulation, and they often focus on predicting different properties. The Monte Carlo simulation is good at predicting equilibrium properties, while the Molecular Dynamics simulation is good at dynamic properties. For the Monte Carlo simulation, the development of efficient algorithms is particularly important. A traditional Monte Carlo molecular simulation includes the following steps: (1) Initialize the system coordinates. (2) Calculate the total energy of the system according to the selected force field and the functional form. (3) Randomly perform a Monte Carlo move to generate a new conformation of the system. (4) Calculate the total energy of the new conformation. (5) Decide whether to accept the move according to the acceptance probability. If yes, the system adopts the new conformation, otherwise, returns to the initial conformation and one continues to repeat steps (3)-(5). In traditional molecular simulation, the most important thing in each step of the simulation process is to calculate the total energy of the system. In the framework of the classical force field, the total intermolecular energy of the system can be expressed as: $E_{Total}=E_{LJ}+E_{Coul}$, where $E_{LJ}$ is Lennard-Jones energy, $E_{Coul}$ is Coulomb energy. The method to calculate Coulomb energy in the frame of classical force field is Coulomb potential $$E_{Coul} = \frac{q_1 q_2}{4\pi\varepsilon_0 r}.$$

It can be seen from the above equation that the Coulomb energy decays as $r^{-1}$ with the distance between molecules. However, in traditional molecular simulations, due to the consideration of periodic boundary conditions, the total number of particles in the system increases as $r^3$ with the size of the system. This results in that if periodic boundary conditions are used, the Coulomb energy will not converge—the total energy of the system tends to infinity, and the simulation cannot be performed. The traditional solution is to use the Ewald sum algorithm for Coulomb energy. This algorithm decomposes the Coulomb energy into two parts. The first part introduces the error function to calculate short-range electrostatic interactions, which can quickly converge. The second part, long range electrostatic interactions, can also converge by doing calculation in the reciprocal space. Thus the problem of non-convergence of Coulomb energy is perfectly solved. However, the calculation of the second part in the reciprocal space is complicate and time-consuming. For Molecular Dynamics simulation, there are more efficient algorithms such as particle mesh Ewald sum. However, for Monte Carlo simulation, which is as important as Molecular Dynamics, is still limited to use traditional Ewald sum calculation due to its underlying mechanism, and the existing efficient algorithms are not applicable. Therefore, for Monte Carlo simulation, there is an urgent need for a more efficient Ewald sum calculation algorithm. Liquid interfacial tension has important applications in chemical engineering. However, it is difficult to measure through experimental methods, especially under high temperature and high pressure, and the accuracy is low. Therefore, molecular simulation is a good alternative method for obtaining liquid phase interfacial tension. In addition, Ewald sum calculation is often the bottle neck in interfacial tension simulations due to the size and shape of the simulation boxes. Consequently, it is of great importance to develop an efficient method to calculate Ewald sum in these simulations.

SUMMARY

The disclosure aims to improve the efficiency of the long-range Coulomb energy calculation in the molecular simulation process, so as to realize an overall more efficient method for simulating the interfacial tension of the liquid phase.

Specifically, the technical solution of this disclosure is:

A Monte Carlo molecular simulation method for efficiently calculating the interfacial tension of water/benzene liquid phase by improving Ewald sum, including the following steps:

Step A: Initialize the simulation: two simulation boxes were prepared, both with size of (30×30×45 Å)-(35×35×55 Å). Then, 1200-2000 water molecules were put on the grid point of the first box, and 230-380 benzene molecules were put on the grid point of the second box; The simulation temperature and pressure were set at T and p.

In the step A, there are two rules for setting the box size: 1. The box length cannot be too small, and must be greater than or equal to twice the cutoff of the Coulomb and vdW interactions. Here, the cutoff is set to 15-17 Å, so the box size should be larger than 30-34 Å. [Reference: M P Allen, D J Tildesley, Computer Simulation of Liquids, Oxford university press, Oxford, 1989]. 2. It cannot be too large, otherwise the calculation is too time-consuming. The box length is set at the minimum possible box size after considering these two factors. The box size can be set to any number larger than the minimum possible box size. However, the larger the box, the more molecules need to be placed and the greater the amount of calculation.

Step B: Select the force field used for simulation. The TraPPE force field was used for benzene molecules, and the TIP4P/2005 force field was used for water molecules.

Step C: Perform Monte Carlo simulation on the two boxes under the canonical ensemble. The essence of Monte Carlo simulation is the Monte Carlo move.

The reason for selecting the force field in Step B is that the TraPPE force field is a united-atom force field that describes the properties of benzene molecules well, and TIP4P/2005 is a force field that describes the properties of water molecules well. We assumed that good two-phase properties can be obtained by using two force fields that describe single phase well respectively. There are also other options for force field selection. For example, one can use all-atomic force fields GAFF or OPLS for benzene, and use force fields such as SPC/E, TIP4P for water molecules.

In the step C, a complete Monte Carlo move includes the following steps:

(1) Randomly select a molecule;
(2) Randomly select a Monte Carlo move; the types of move here include translation and rotation, and each type of move was given a selection probability of 20-40%;
(3) Execute the selected moves to generate a new conformation;
(4) Calculate the energy of the new conformation, including the intramolecular energy $E_{intra}$, the intermolecular van der Waals energy $E_{vdW}$, the intermolecular short-range Coulomb energy $E_{short}$, and the intermolecular long-range Coulomb energy $E_{long}$, the specific steps are:

Step a: Calculate intramolecular energy:

$$E_{intra} = E_{bond} + E_{angle} + E_{dihedral}$$

where $E_{bond}$ is the bond-stretching energy, $E_{angle}$ is the angle strain energy, $E_{dihedral}$ is the dihedral torsion energy.

Step b: Calculate the intermolecular van der Waals energy:

$$E_{vdW} = \sum_{i,j} 4\varepsilon \left[ \left(\frac{\sigma}{r_{ij}}\right)^{12} - \left(\frac{\sigma}{r_{ij}}\right)^{6} \right]$$

where $\sigma$ and $\varepsilon$ are the LJ force field parameters, and $r_{ij}$ is the distance between particles.

Step c: Calculate the intermolecular short-range Coulomb energy:

$$E_{short} = \frac{1}{4\pi\varepsilon_0} \frac{1}{2} \sum_n \sum_i \sum_j \frac{q_i q_j}{|r_i - r_j + nL|} \text{erfc}\left(\frac{|r_i - r_j + nL|}{\sqrt{2}\sigma}\right)$$

where $\varepsilon_0$ is the vacuum dielectric constant, $q_i$, $q_j$ are the charges of particles i and j, $r_i$, $r_j$ are the particle position vectors, n is the period vector, and L is the box length.

Step d: Calculate the intermolecular long-range Coulomb energy by Ewald sum including the following steps:

Step d1: Calculate the 6 basic trigonometric function values of each particle $$\cos\left(\frac{2\pi}{L_x} r_{xi}\right), \cos\left(\frac{2\pi}{L_y} r_{yi}\right), \cos\left(\frac{2\pi}{L_z} r_{zi}\right), \sin\left(\frac{2\pi}{L_x} r_{xi}\right), \sin\left(\frac{2\pi}{L_y} r_{yi}\right), \sin\left(\frac{2\pi}{L_z} r_{zi}\right);$$

where $r_{xi}$, $r_{yi}$, $r_{zi}$ are the coordinates of the particle i in x, y, and z directions, $L_x$, $L_y$, $L_z$ are the box lengths in x, y, and z directions.

Step d2: Through recursion and the basic arithmetic operations, all remaining trigonometric function values that need to be calculated can be obtained.

$$\sin\left(\frac{2\pi l}{L_x} r_{xi} + \frac{2\pi m}{L_y} r_{yi} + \frac{2\pi n}{L_z} r_{zi}\right) \text{ and } \cos\left(\frac{2\pi l}{L_x} r_{xi} + \frac{2\pi m}{L_y} r_{yi} + \frac{2\pi n}{L_z} r_{zi}\right)$$

where each group of (l, m, n) is the reciprocal space vector and (l, m, n) are three integers, the absolute value of l, m, and n do not exceed $K_{max,i} = \text{int}(\kappa L_i) + 1$, wherein $\kappa = 3.2/R_c$, $R_c$ is the cutoff of the system, $L_i$ is the box length in each direction.

Step d3: Calculate the total long-range Coulomb interaction energy after obtaining all trigonometric function values:

$$E_{long} = C_0 \sum_{l=-l_{max}, l_{max}} \sum_{m=-m_{max}, m_{max}} \sum_{n=-n_{max}, n_{max}}$$

$$\left[ \left(\sum_i q_i \cos\left(\frac{2\pi l}{L_x} r_{xi} + \frac{2\pi m}{L_y} r_{yi} + \frac{2\pi n}{L_z} r_{zi}\right)\right)^2 + \left(\sum_i q_i \sin\left(\frac{2\pi l}{L_x} r_{xi} + \frac{2\pi m}{L_y} r_{yi} + \frac{2\pi n}{L_z} r_{zi}\right)\right)^2 \right]$$

Calculate the acceptance probability according to the new energy of the system.

$$P_{acc} = \min\{1, \exp[-\beta(E_{new} - E_{old})]\}$$

where $E_{new}$ is the energy of the new conformation and $E_{old}$ is the energy of the old conformation; Then, a random number was generated. If the random number is less than $P_{acc}$, the new conformation is accepted; otherwise it will not be accepted, and the system returns to the old conformation. The range of random number in determining which molecule to move is [1, N], where N is the number of molecules, and the range of random number to determine whether to accept the move is (0, 1).

The above is a complete Monte Carlo move, and it is repeated until 50,000 Monte Carlo cycles are completed (a cycle contains N Monte Carlo moves, where N is the number of molecules in the system) to achieve the goal of equilibrating the system.

The simulation before merging the boxes has only two kinds of moves for water and benzene, which are translation and rotation. Each of the moves is given a 50% probability. Volume move is added after the two boxes were merged.

The criteria to judge whether the system reaches equilibrium is that some system properties do not have a large drift as the simulation is running, but fluctuate around a certain value. These properties can be the total energy of the system, the total volume of the system, the total pressure, or the value of the interfacial tension that we care about. For the simulation before the merger of the two boxes, there is no concept of interfacial tension or volume change, so the total energy of the system can be used to monitor the equilibrium. After the two boxes are merged, the three types of moves are allocated as follows: volume move was given 0.1% probability and the other two (translation and rotation) moves were assigned half of the remaining probability respectively. At this time, the equilibrium conditions can also include the total volume of the system, the total pressure, and the change of the interfacial tension.

In the step C, molecules were randomly selected for both simulation boxes. These two boxes can be regarded as two independent simulations and they used the same set of Monte Carlo moves; here random selection means, for example, if one wants to randomly select one water molecule from 1500 water molecules during one Monte Carlo move; the computer will generate a random integer between 1 and 1500 to determine which water molecule to move. The water molecule whose index is the same with the above random integer will be chosen.

Step D: Join the water box and the benzene box along the z direction to form a large box of (30×30×90 Å)-(35×35×110 Å), and the Monte Carlo cycle mentioned in step C were repeated for 50000-80000 times to equilibrate the system; During the equilibrium stage, the simulation was performed under isothermal-isobaric ensemble, and a new type of Monte Carlo move was added, which is the volume change of the system.

Step E: After the system reaches equilibrium, data were collected during the production period. The Monte Carlo cycle mentioned in step C was repeated for 400000-500000 times under the isothermal-isobaric ensemble, and the interfacial tension was calculated for every 5 cycles. The final interfacial tension result is the statistical average of all collected data.

In addition to providing a commonly used process for molecular simulation, this disclosure improves the calculation method of the Ewald sum part. After using the Ewald sum calculation method of this disclosure, the overall simulation efficiency can be increased by about 20%.

DESCRIPTION OF THE EMBODIMENTS

The preferred embodiments of this disclosure will be described in further detail below:

Embodiment 1

Figure 1:
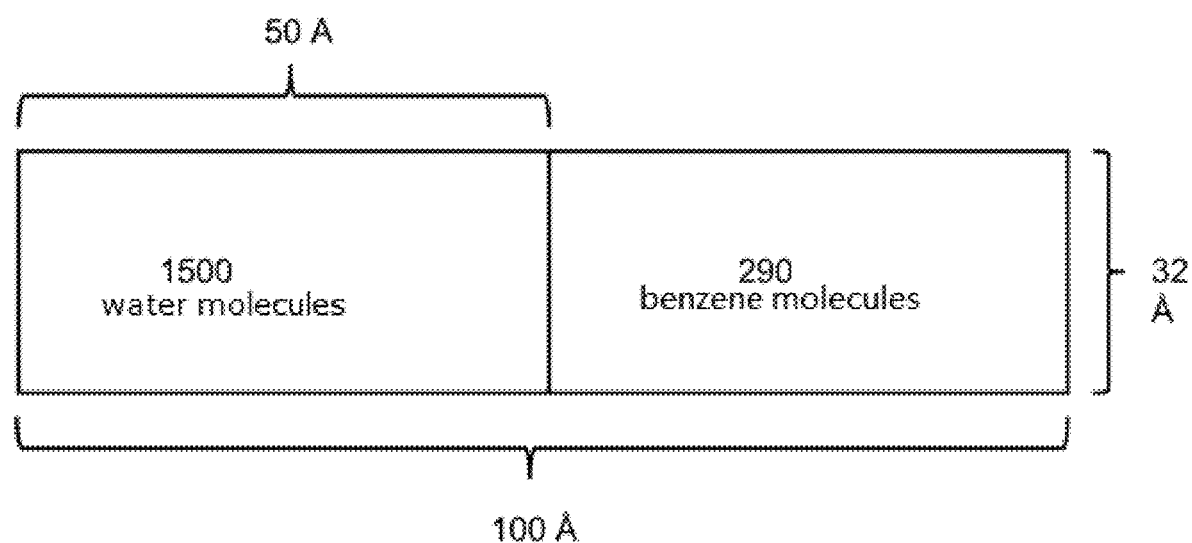
FIG. 1 is Monte Carlo simulation schematic diagram of liquid phase interfacial tension.

An improved Ewald sum Monte Carlo molecular simulation method for efficiently calculating the interfacial tension of water/benzene liquid phase, as shown in FIG. 1, includes the following steps:

Step A: Initialize the simulation: two simulation boxes were prepared, each with a size of 32×32×50 Å. Then, 1500 water molecules were put on the grid point of the first box, and 290 benzene molecules were put on the grid point of the second box. In this example, the applicant selected four systems with different temperatures and pressures for the simulation, which were 1. T=298 K, p=1 bar. 2. T=323 K, p=1 bar. 3. T=423 K, p=400 bar. 4. T=473 K, p=400 bar. The only difference between the four systems is the temperature and the pressure, and the following steps are the same.

Step B: Select the force field used for simulation: benzene molecules were modeled with the TraPPE force field, and TIP4P/2005 force field was used for water molecules.

Step C: Perform Monte Carlo simulation on the two boxes under the canonical ensemble. The core of Monte Carlo simulation is the Monte Carlo move. A complete Monte Carlo move includes the following steps:

Step C1: Randomly select a molecule;

Step C2 Randomly select a Monte Carlo move type; the types of move here include translation and rotation, and each type of the moves was given a selection probability of 50%;

Step C3 Execute the selected moves to generate a new conformation;

In the step C3, calculate the new energy of the system, including the intramolecular energy $E_{intra}$, the intermolecular van der Waals energy $E_{vdW}$, the intermolecular short-range Coulomb energy $E_{short}$, and the intermolecular long-range Coulomb energy $E_{long}$, the specific steps are:

Step a: Calculate intramolecular energy $$E_{intra}=E_{bond}+E_{angle}+E_{dihedral}$$

where $E_{bond}$ is the bond stretching energy, $E_{angle}$ is the angle strain energy, $E_{dihedral}$ is the dihedral torsion energy.

Step b: Calculate the intermolecular van der Waals energy $$E_{vdW} = \sum_{i,j} 4\varepsilon\left[\left(\frac{\sigma}{r_{ij}}\right)^{12} - \left(\frac{\sigma}{r_{ij}}\right)^6\right]$$

where $\sigma$ and $\varepsilon$ are the force field parameters, and $r_{ij}$ is the distance between particles.

Step c: Calculate the intermolecular short-range Coulomb energy $$E_{short} = \frac{1}{4\pi\varepsilon_0}\frac{1}{2}\sum_n\sum_i\sum_j \frac{q_iq_j}{|r_i-r_j+nL|}\text{erfc}\left(\frac{|r_i-r_j+nL|}{\sqrt{2}\sigma}\right)$$

Where $\varepsilon_0$ is the vacuum dielectric constant, $q_i$, $q_j$ are the charges of particles i and j, $r_i$, $r_j$ are the particle position vectors, n is the period vector, and L is the box length.

Step d: Calculate the intermolecular long-range Coulomb energy by Ewald sum, which includes the following steps:

Step d1: Calculate the 6 basic trigonometric function values of each particle $$\cos\left(\frac{2\pi}{L_x}r_{xi}\right), \cos\left(\frac{2\pi}{L_y}r_{yi}\right), \cos\left(\frac{2\pi}{L_z}r_{zi}\right), \sin\left(\frac{2\pi}{L_x}r_{xi}\right), \sin\left(\frac{2\pi}{L_y}r_{yi}\right), \sin\left(\frac{2\pi}{L_z}r_{zi}\right);$$

where $r_{xi}$, $r_{yi}$, $r_{zi}$ are the coordinates of the particle in i in x, y, and z directions, $L_x$, $L_y$, $L_z$ are the box lengths in x, y, and z directions.

Step d2: Through recursion and the basic arithmetic operations, the remaining trigonometric function values that need to be calculated were obtained.

$$\sin\left(\frac{2\pi l}{L_x}r_{xi} + \frac{2\pi m}{L_y}r_{yi} + \frac{2\pi n}{L_z}r_{zi}\right) \text{ and } \cos\left(\frac{2\pi l}{L_x}r_{xi} + \frac{2\pi m}{L_y}r_{yi} + \frac{2\pi n}{L_z}r_{zi}\right)$$

where each group of (l, m, n) is a reciprocal space vector. The reciprocal space vector (l, m, n) is composed of three integers, and the absolute value of each integer can not exceed $K_{max,i}=\text{int}(\kappa L_i)+1$, wherein $\kappa=3.2/R_c$, $R_c$ is the cutoff of the system, $L_i$ is the box length in each direction. In this Embodiment, $K_{max,x}=K_{max,y}=$int (3.2/16*32)+1=7, $K_{max,z}=$int (3.2/16*50)+1=11.

Step d3: Calculate the total long-range Coulomb interaction energy after obtaining all trigonometric function values:

$$E_{long} = C_0 \Sigma_{l=-l_{max},l_{max}} \Sigma_{m=-m_{max},m_{max}}$$

$$\Sigma_{n=-n_{max},n_{max}} \left[ \left( \Sigma_i q_i \cos\left(\frac{2\pi l}{L_x} r_{xi} + \frac{2\pi m}{L_y} r_{yi} + \frac{2\pi n}{L_z} r_{zi}\right) \right)^2 + \left( \Sigma_i q_i \sin\left(\frac{2\pi l}{L_x} r_{xi} + \frac{2\pi m}{L_y} r_{yi} + \frac{2\pi n}{L_z} r_{zi}\right) \right)^2 \right]$$

Calculate the acceptance probability according to the new energy of the system:

$$P_{acc} = \min\{1, \exp[-\beta(E_{new} - E_{old})]\}$$

where $E_{new}$ is the energy of the new conformation and $E_{old}$ is the energy of the old conformation.

Then, a random number was generated. If the random number is less than $P_{acc}$, the new conformation is accepted; otherwise it will not be accepted, and the system returns to the old conformation.

The steps define a complete Monte Carlo move. The above steps were repeated for 50,000 cycles (a cycle contains N Monte Carlo moves, where N is the number of molecules in the system) to equilibrate the system.

In the step C, randomly select a molecule with equal probability for both two boxes. These two boxes can be regarded as two independent simulations, and they used the same set of Monte Carlo move; random selection means, for example, if one wants to randomly select one water molecule for a Monte Carlo move from 1500 water molecules, the computer will generate a random integer between 1 and 1500 to determine which water molecule is chosen to move.

Figure 2:
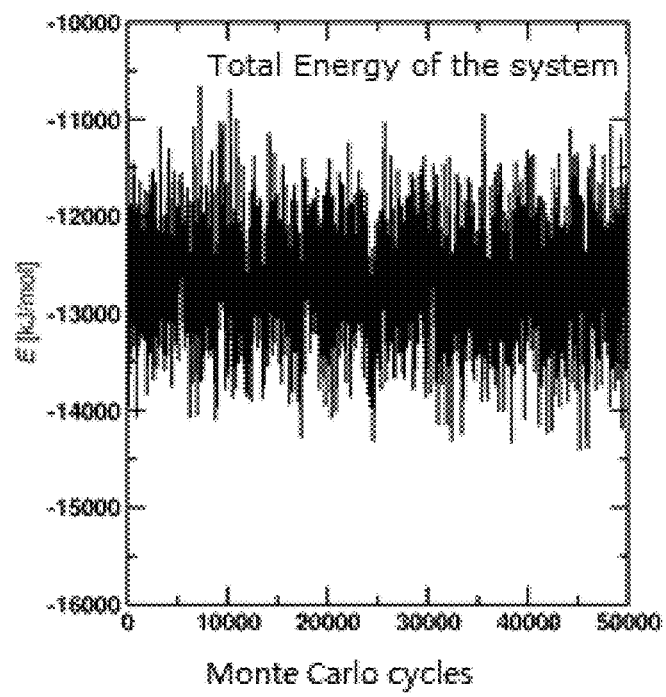
FIG. 2 shows that the simulation system has reached equilibrium—the total energy of the system fluctuates around a certain value as the simulation progresses (Monte Carlo cycle).

Step D: Join the water box and the benzene box along the z direction to form a large box of (32×32×100 Å), and the Monte Carlo cycle mentioned in step C was repeated 50000 times to equilibrate the system as shown in FIG. 2. During the equilibrium stage, the simulation was performed under isothermal-isobaric ensemble, and a new type of Monte Carlo move was added, which is the volume change of the system.

Step E: After the system reached equilibrium, the data were collected during the production stage. The Monte Carlo cycle mentioned in step C was repeated for 400000 times under the isothermal-isobaric ensemble, and the interfacial tension was calculated for every 5 cycles. The final interfacial tension result is the statistical average of all results. Here, the interfacial tension is calculated as:

$$\gamma_{KB} = \frac{1}{2} \langle P_N - P_T \rangle L_z$$

Where $L_z = 100$ Å in this embodiment.

The calculation of the total energy could be $E_{Total} = E_{inter} + E_{intra}$, wherein the first term is an intermolecular energy, and the second term is an intramolecular energy. The present disclosure is concerned with the intermolecular energy, which could be written as $E_{inter} = E_{LJ} + E_{Coul}$, wherein the first term is a vdW energy, and the second term is a Coulomb energy. The present disclosure is concerned with the Coulomb energy. The calculation of Coulomb energy can be decomposed into $E_{Coul} = E_{short} + E_{long} + E_{self}$ where $E_{short}$ has been described in the technical problem and the defect, that is, the first term of the formula below.

$$E_{Coul} = \frac{1}{4\pi\varepsilon_0} \frac{1}{2} \sum_n \sum_i \sum_j \frac{q_i q_j}{|r_i - r_j + nL|} \text{erfc}\left(\frac{|r_i - r_j + nL|}{\sqrt{2}\sigma}\right) +$$

$$\frac{1}{2V\varepsilon_0} \sum_{k \neq 0} \frac{e^{-\sigma^2 k^2/2}}{k^2} |S(k)|^2 - \frac{1}{4\pi\varepsilon_0} \frac{1}{\sqrt{2\pi}\sigma} \sum_i q_i^2 \quad E_{Coul} =$$

$$\frac{1}{4\pi\varepsilon_0} \frac{1}{2} \sum_n \sum_i \sum_j \frac{q_i q_j}{|r_i - r_j + nL|} \text{erfc}\left(\frac{|r_i - r_j + nL|}{\sqrt{2}\sigma}\right) +$$

$$\frac{1}{2V\varepsilon_0} \sum_{k \neq 0} \frac{e^{-\sigma^2 k^2/2}}{k^2} |S(k)|^2 - \frac{1}{4\pi\varepsilon_0} \frac{1}{\sqrt{2\pi}\sigma} \sum_i q_i^2$$

The energy expression in molecular simulation is usually $E_{Total} = E_{LJ} + E_{Coul} + E_{intra}$, where $E_{LJ}$ is Lennard Jones energy, $E_{Coul}$ is Coulomb energy and $E_{Intra}$ is intramolecular energy. The calculation of Coulomb energy can be further decomposed into $E_{Coul} = E_{short} + E_{long}$, where $E_{short}$ is the short-range interaction energy, $E_{long}$ is the long-range interaction energy, and $E_{self}$ is the self-interaction energy, and can be expressed as, $$E_{Coul} = \frac{1}{4\pi\varepsilon_0} \frac{1}{2} \sum_n \sum_i \sum_j \frac{q_i q_j}{|r_i - r_j + nL|} \text{erfc}\left(\frac{|r_i - r_j + nL|}{\sqrt{2}\sigma}\right) +$$

$$\frac{1}{2V\varepsilon_0} \sum_{k \neq 0} \frac{e^{-\sigma^2 k^2/2}}{k^2} |S(k)|^2 - \frac{1}{4\pi\varepsilon_0} \frac{1}{\sqrt{2\pi}\sigma} \sum_i q_i^2$$

where, the first term is the short-range interaction, the second is the long-range interaction, and the last term is the self-interaction.

$E_{long}$ is the main improvement of this disclosure. The long-range Coulomb interaction energy using Ewald sum can be further written as:

$$E_{long} = C_0 \Sigma_{l=-l_{max},l_{max}} \Sigma_{m=-m_{max},m_{max}}$$

$$\Sigma_{n=-n_{max},n_{max}} \left[ \left( \Sigma_i q_i \cos\left(\frac{2\pi l}{L_x} r_{xi} + \frac{2\pi m}{L_y} r_{yi} + \frac{2\pi n}{L_z} r_{zi}\right) \right)^2 + \left( \Sigma_i q_i \sin\left(\frac{2\pi l}{L_x} r_{xi} + \frac{2\pi m}{L_y} r_{yi} + \frac{2\pi n}{L_z} r_{zi}\right) \right)^2 \right]$$

where $C_0$ is a constant, l, m, n are the reciprocal space vectors, $l_{max}$, $m_{max}$, $n_{max}$ are the maximum values that the reciprocal space vector can take, $L_x$, $L_y$, $L_z$ are the box lengths in x, y, and z directions, $q_i$ is the charge of the particle i, $r_{xi}$, $r_{yi}$, $r_{zi}$ are the coordinates of the particle i. The triple summation indices l, m and n are integers, and l, m, n values between adjacent summations only differ by 1. Therefore, the calculation of this term can be simplified through Sum to Product Identities.

Embodiment 2

When calculating the summation term $l = l_0 + 1$, $m = m_0$, $n = n_0$, the applicant found that it can be deduced from the value of trigonometric functions when $l = l_0$ with the basic arithmetic operations, $$\cos\left(\frac{2\pi(l_0+1)}{L_x}r_{xi} + \frac{2\pi m_0}{L_y}r_{yi} + \frac{2\pi n_0}{L_z}r_{zi}\right) =$$

$$\cos\left(\frac{2\pi l_0}{L_x}r_{xi} + \frac{2\pi m_0}{L_y}r_{yi} + \frac{2\pi n_0}{L_z}r_{zi}\right)\cos\left(\frac{2\pi}{L_x}r_{xi}\right) -$$

$$\sin\left(\frac{2\pi l_0}{L_x}r_{xi} + \frac{2\pi m_0}{L_y}r_{yi} + \frac{2\pi n_0}{L_z}r_{zi}\right)\sin\left(\frac{2\pi}{L_x}r_{xi}\right)$$

Similarly, when calculating another trigonometric function, recursion can be used as:

$$\sin\left(\frac{2\pi(l_0+1)}{L_x}r_{xi} + \frac{2\pi m_0}{L_y}r_{yi} + \frac{2\pi n_0}{L_z}r_{zi}\right) =$$

$$\sin\left(\frac{2\pi l_0}{L_x}r_{xi} + \frac{2\pi m_0}{L_y}r_{yi} + \frac{2\pi n_0}{L_z}r_{zi}\right)\cos\left(\frac{2\pi}{L_x}r_{xi}\right) +$$

$$\cos\left(\frac{2\pi l_0}{L_x}r_{xi} + \frac{2\pi m_0}{L_y}r_{yi} + \frac{2\pi n_0}{L_z}r_{zi}\right)\sin\left(\frac{2\pi}{L_x}r_{xi}\right)$$

If one continues this recursion, the applicant found that the trigonometric function values that need to be calculated explicitly for the triple summation consist only the 6 terms $$\cos\left(\frac{2\pi}{L_x}r_{xi}\right), \cos\left(\frac{2\pi}{L_y}r_{yi}\right), \cos\left(\frac{2\pi}{L_z}r_{zi}\right), \sin\left(\frac{2\pi}{L_x}r_{xi}\right), \sin\left(\frac{2\pi}{L_y}r_{yi}\right), \sin\left(\frac{2\pi}{L_z}r_{zi}\right).$$

Therefore, the complexity of calculating trigonometric functions is simplified from $L*M*N*N_0$ to $6*N_0$. In the actual molecular simulation process, $L*M*N$ is often much larger than 6, so this method can significantly improve the efficiency. Consequently, the program is rewritten to generate a more efficient Ewald sum calculation subroutine as ewald_sum_recursion.

TABLE 1

Simulated and experimental values of water/benzene interfacial tension in Embodiment 1

| system | 1 | 2 | 3 | 4 |
|---|---|---|---|---|
| temperature (K) | 298 | 323 | 423 | 473 |
| pressure (bar) | 1 | 1 | 400 | 400 |
| Simulated interfacial tension (dyn/cm) | 50.4 ± 1.5 | 48.9 ± 1.7 | 39.5 ± 1.3 | 33.1 ± 1.0 |
| Literature experimental value (dyn/cm) | 50.5 | 47.78 | 36.09 | 30.59 |

[References for interfacial tension literature values: (1) S. Zeppieri, J. Rodriguez, A. L. Lopez de Ramos, Interfacial tension of alkane+water systems, *J. Chem. Eng. Data* 46 (2001) 1086-1088 (2) G. Wiegand, E. U. Franck, Interfacial tension between water and non-polar fluids up to 473 K and 2800 bar, *Ber. Bunsen. Phys. Chem.* 98 (1994) 809-817. (3) H. Y. Jennings Jr., The effect of temperature and pressure on the interfacial tension of benzene-water and normal decane-water, *J. Colloid Interface Sci.* 24 (1967) 323-329.]

TABLE 2

Comparison of calculation efficiency of new and old algorithms

| | Time per Monte Carlo cycle with the new algorithm (s) | Time per Monte Carlo cycle with the old algorithm (s) | Efficiency improvement percentage (%) |
|---|---|---|---|
| Water/benzene interfacial tension | 4.81 | 6.09 | 21.0 |

Figure 3:
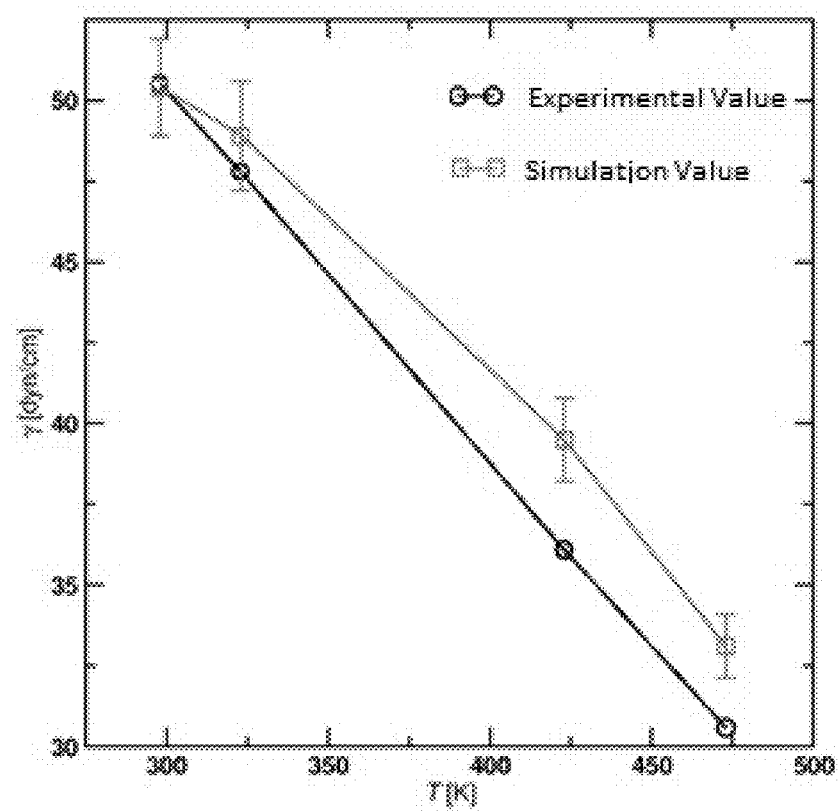
FIG. 3 is the comparison of the water/benzene interfacial tension values obtained by simulation using the method of this disclosure and the experimental values in literature. The black circles are the experimental values, the red squares are the simulation values, and the red interval is the uncertainty of the simulation value.

Table 1 and FIG. 3 show the comparison between the water/benzene liquid phase interfacial tension value simulated by the method of this disclosure and the experimental value in the literature. It can be seen from Table 1 and FIG. 3 that the interfacial tension value obtained by the simulation of this disclosure is in good agreement with the experimental value of the literature under different temperature and pressure.

Table 2 shows the simulation of the water/benzene interfacial tension of the present disclosure by using the new algorithm and the old algorithm, respectively used to calculate an average time for performing Monte Carlo cycle. Unlike the old method that all trigonometric function values need to be calculated explicitly, the results show that the new method improved the computational efficiency by 21% as shown in the table above. This is because a large number of reciprocal space vectors l, m, and n are not explicitly calculated using trigonometric functions but deduced using basic arithmetic operations.

The above content is a further detailed description of this disclosure in combination with specific preferred embodiments, and it cannot be considered that the specific implementation of this disclosure is limited to these descriptions. For the ordinary technical staff in the technical field of this disclosure, a number of simple deductions or substitutions can be made without departing from the concept of this disclosure, which should be regarded as falling within the protection scope of this disclosure.

What is claimed is:

1. An efficient Monte Carlo molecular simulation method for calculating a liquid phase interfacial tension between benzene and water by improving Ewald sum, comprising:
   Step A: initializing the molecular simulation: preparing two simulation boxes with a size of (30×30×45 Å)-(35×35×55 Å) for each box, putting 1200-2000 water molecules on grid point of the first box, 230-380 benzene molecules on grid point of the second box; then, selecting simulation temperature T and pressure p;
   Step B: selecting the force field used for simulation: using the TraPPE force field for benzene molecules, and using the TIP4P/2005 force field for water molecules;
   Step C: performing Monte Carlo simulations on the two boxes separately under a canonical ensemble, wherein the Monte Carlo simulation contains at least one Monte Carlo move;
   Step D: joining the water box and the benzene box along the z direction to form a large box of (30×30×90 Å)-(35×35×110 Å), and running the Monte Carlo simulation mentioned in the step C for 50000-80000 Monte Carlo cycles to reach equilibrium, wherein a Monte Carlo cycle contains N Monte Carlo moves, where N is a number of molecules, wherein reaching equilibrium is determined if at least one given property fluctuate around a certain value as the simulation is running; and Step E: after reaching equilibrium, running the Monte Carlo simulation under an isothermal-isobaric ensemble for 400000-500000 Monte Carlo cycles, so as to obtain an interfacial tension for every 5 Monte Carlo cycles, and obtaining a liquid phase interfacial tension between benzene and water by averaging the calculated interfacial tensions.

2. The molecular simulation method according to claim 1, wherein a complete Monte Carlo move in the step C includes the following steps:
(1) randomly selecting a molecule, comprising: generating, by computer, a random integer between 1 and N to determine which molecule to move, and selecting a molecule whose index is the same with the random integer;
(2) randomly selecting a Monte Carlo move; types of move here include translation and rotation, and each type of the moves is given a selection probability of 20-40%;
(3) moving the selected molecule according to the selected Monte Carlo move to generate a new conformation;
(4) calculating energy of the new conformation, including an intramolecular energy $E_{intra}$, an intermolecular van der Waals energy $E_{vdW}$, an intermolecular short-range Coulomb energy $E_{short}$, and an intermolecular long-range Coulomb energy $E_{long}$, the specific steps are:

Step a: calculating the intramolecular energy:

$$E_{intra} = E_{bond} + E_{angle} + E_{dihedral},$$

where $E_{bond}$ is bond energy, $E_{angle}$ is angle strain energy, $E_{dihedral}$ is dihedral torsion energy;

Step b: calculating the intermolecular van der Waals energy:

$$E_{vdW} = \Sigma_{i,j} 4\varepsilon \left[ \left(\frac{\sigma}{r_{ij}}\right)^{12} - \left(\frac{\sigma}{r_{ij}}\right)^{6} \right],$$

where $\sigma$ and $\varepsilon$ are the force field parameters, and $r_{ij}$ is a distance between particles;

Step c: calculating the intermolecular short-range Coulomb energy:

$$E_{short} = \frac{1}{4\pi\varepsilon_0} \frac{1}{2} \Sigma_n \Sigma_i \Sigma_j \frac{q_i q_j}{|r_i - r_j + nL|} \mathrm{erfc}\left(\frac{|r_i - r_j + nL|}{\sqrt{2}\sigma}\right),$$

where $\varepsilon_0$ is a vacuum dielectric constant, $q_i$, $q_j$ are charges of particles i and j, $r_i$, $r_j$ are particle position vectors, n is a period vector, and L is a box length;

Step d: calculating the intermolecular long-range Coulomb energy by Ewald sum including the following steps:

Step d1: calculating 6 basic trigonometric function values of each particle $$\cos\left(\frac{2\pi}{L_x}r_{xi}\right), \cos\left(\frac{2\pi}{L_y}r_{yi}\right), \cos\left(\frac{2\pi}{L_z}r_{zi}\right), \sin\left(\frac{2\pi}{L_x}r_{xi}\right), \sin\left(\frac{2\pi}{L_y}r_{yi}\right), \sin\left(\frac{2\pi}{L_z}r_{zi}\right);$$

where $r_{xi}$, $r_{yi}$, $r_{zi}$ are coordinates of a particle i in x, y, and z directions, $L_x$, $L_y$, $L_z$ are box lengths in x, y, and z directions;

Step d2: through recursion and basic arithmetic operations to indirectly obtain the remaining trigonometric function values that need to be calculated;

$$\sin\left(\frac{2\pi l}{L_x}r_{xi} + \frac{2\pi m}{L_y}r_{yi} + \frac{2\pi n}{L_z}r_{zi}\right) \text{ and } \cos\left(\frac{2\pi l}{L_x}r_{xi} + \frac{2\pi m}{L_y}r_{yi} + \frac{2\pi n}{L_z}r_{zi}\right),$$

where each group of (l, m, n) is a reciprocal space vector and the reciprocal space vector (l, m, n) is composed of three integers, the absolute value of the vector in each dimension does not exceed $K_{max,i} = \mathrm{int}(\kappa L_i)+1$, wherein $\kappa = 3.2/Rc$, Rc is a cutoff, $L_i$ is the box length in each direction;

Step d3: calculating a total long-range Coulomb interaction energy after obtaining all trigonometric function values:

$$E_{long} = C_0 \Sigma_{l=-l_{max},l_{max}} \Sigma_{m=-m_{max},m_{max}}$$

$$\Sigma_{n=-n_{max},n_{max}} \left[ \left( \Sigma_i q_i \cos\left(\frac{2\pi l}{L_x}r_{xi} + \frac{2\pi m}{L_y}r_{yi} + \frac{2\pi n}{L_z}r_{zi}\right) \right)^2 + \left( \Sigma_i q_i \sin\left(\frac{2\pi l}{L_x}r_{xi} + \frac{2\pi m}{L_y}r_{yi} + \frac{2\pi n}{L_z}r_{zi}\right) \right)^2 \right]$$

(5) calculating an acceptance probability according to energy of the new conformation: $P_{acc} = \min\{1, \exp[-\beta(E_{new} - E_{old})]\}$, and generate a random number;
where $E_{new}$ is energy of the new conformation and $E_{old}$ is energy of the old conformation; then a random number is generated,
if the random number is less than the acceptance probability $P_{acc}$, the new conformation is accepted; otherwise it is rejected, and the old conformation is restored.

3. The molecular simulation method according to claim 1, wherein the calculation method of interfacial tension in the step E is defined by Kirkwood and Buff:

$$\gamma_{KB} = \frac{1}{2}\langle P_N - P_T \rangle L_z,$$

where $L_z$ is a box length in z direction, $P_N$, $P_T$ are a pressure in the normal and tangential directions respectively, the factor ½ is adopted accounting for the two interfaces;
a general method to calculate pressure here is:

$$p = \frac{k_B T N}{V} + \frac{1}{3V} \Sigma f_{ij} r_{ij},$$

where $k_B$ is Boltzmann's constant, T is a temperature, N is a number of molecules, V is a volume, $f_{ij}$ is a force vector between particles of i and j, and $r_{ij}$ is a distance vector.

4. A method for predicting a liquid phase interfacial tension between benzene and water, implemented by a computer, comprising:
Step A: initializing the molecular simulation: two simulation boxes were prepared, both with the size of (30×30×45 Å)-(35×35×55 Å), and 1200-2000 water molecules were put on the grid point of the first box, 230-380 benzene molecules were put on the grid point of the second box; then, the simulation temperature T and pressure p were set;

Step B: selecting the force field used for simulation: the TraPPE force field was used for benzene molecules, and the TIP4P/2005 force field was used for water molecules;

Step C: performing Monte Carlo simulations on the two boxes separately under a canonical ensemble, the Monte Carlo simulation containing at least one Monte Carlo move;

Step D: joining the water box and the benzene box along the z direction to form a large box of (30×30×90 Å)-(35×35×110 Å), and run the Monte Carlo simulation mentioned in the step C for 50000-80000 Monte Carlo cycles to reach equilibrium, wherein reaching equilibrium is determined if at least one given property fluctuate around a certain value as the simulation is running; and Step E: after reaching equilibrium, running the Monte Carlo simulation under an isothermal-isobaric ensemble for 400000-500000 Monte Carlo cycles so as to obtain an interfacial tension for every 5 Monte Carlo cycles, and obtain a liquid phase interfacial tension between benzene and water according to the calculated interfacial tensions;

wherein the Monte Carlo move comprises:
(1) randomly selecting a molecule;
(2) randomly selecting a Monte Carlo move; types of move here include translation and rotation, and each type of the moves was given a selection probability of 20-40%;
(3) moving the selected molecule according to the selected Monte Carlo move to generate a new conformation;
(4) obtaining energy of the new conformation, including an intramolecular energy, an intermolecular van der Waals energy, an intermolecular short-range Coulomb energy, and an intermolecular long-range Coulomb energy; and
(5) determining, according to the energy of the new conformation, whether the new conformation is accepted.

5. The method of claim 4, wherein the intermolecular long-range Coulomb energy is calculated by Ewald sum including the following steps:

Step d1: calculating 6 basic trigonometric function values of each particle $$\cos\left(\frac{2\pi}{L_x}r_{xi}\right), \cos\left(\frac{2\pi}{L_y}r_{yi}\right), \cos\left(\frac{2\pi}{L_z}r_{zi}\right), \sin\left(\frac{2\pi}{L_x}r_{xi}\right), \sin\left(\frac{2\pi}{L_y}r_{yi}\right), \sin\left(\frac{2\pi}{L_z}r_{zi}\right);$$

where $r_{xi}$, $r_{yi}$, $r_{zi}$ are coordinates of a particle i in x, y, and z directions, $L_x$, $L_y$, $L_z$ are box lengths in x, y, and z directions;

Step $d_2$: indirectly obtaining the remaining trigonometric function values that need to be calculated through recursion and basic arithmetic operations;

$$\sin\left(\frac{2\pi l}{L_x}r_{xi} + \frac{2\pi m}{L_y}r_{yi} + \frac{2\pi n}{L_z}r_{zi}\right) \text{ and } \cos\left(\frac{2\pi l}{L_x}r_{xi} + \frac{2\pi m}{L_y}r_{yi} + \frac{2\pi n}{L_z}r_{zi}\right),$$

where each group of (l, m, n) is a reciprocal space vector and the reciprocal space vector (l, m, n) is composed of three integers, the absolute value of the vector in each dimension does not exceed $K_{max,i}=\text{int}(\kappa L_i)+1$, wherein $k=3.2/R_c$, $R_c$ is a cutoff, $L_i$ is the box length in each direction;

Step d3: calculating a total long-range Coulomb interaction energy after obtaining all trigonometric function values:

$$E_{long} = C_0 \sum_{l=-l_{max},l_{max}} \sum_{m=-m_{max},m_{max}}$$
$$\sum_{n=-n_{max},n_{max}} \left[\left(\sum_i q_i \cos\left(\frac{2\pi l}{L_x}r_{xi} + \frac{2\pi m}{L_y}r_{yi} + \frac{2\pi n}{L_z}r_{zi}\right)\right)^2 + \left(\sum_i q_i \sin\left(\frac{2\pi l}{L_x}r_{xi} + \frac{2\pi m}{L_y}r_{yi} + \frac{2\pi n}{L_z}r_{zi}\right)\right)^2\right].$$

6. The method of claim 4, wherein said Monte Carlo simulations on the two boxes separately use the same type of Monte Carlo move which is randomly selected from translation and rotation.

7. The method of claim 4, wherein a Monte Carlo move for the Monte Carlo simulation on the large box is randomly selected from translation, rotation and volume move.

8. The method of claim 4, wherein the property is selected from total energy, total volume, total pressure and change of the interfacial tension.

* * * * *